(12) United States Patent
Tsao et al.

(10) Patent No.: US 9,514,521 B2
(45) Date of Patent: Dec. 6, 2016

(54) DIAGNOSTIC ULTRASOUND APPARATUS

(71) Applicant: HITACHI ALOKA MEDICAL, LTD., Mitaka-shi, Tokyo (JP)

(72) Inventors: Jing-Wen Tsao, Mitaka (JP); Shingo Yoshizawa, Mitaka (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 14/380,290

(22) PCT Filed: Feb. 19, 2013

(86) PCT No.: PCT/JP2013/054015
§ 371 (c)(1),
(2) Date: Aug. 21, 2014

(87) PCT Pub. No.: WO2013/129185
PCT Pub. Date: Sep. 6, 2013

(65) Prior Publication Data
US 2015/0016744 A1    Jan. 15, 2015

(30) Foreign Application Priority Data

Mar. 1, 2012  (JP) .................................. 2012-045280
Mar. 1, 2012  (JP) .................................. 2012-045282

(51) Int. Cl.
*G06T 5/00*   (2006.01)
*A61B 8/08*   (2006.01)
*G01S 7/52*   (2006.01)

(52) U.S. Cl.
CPC ............. *G06T 5/003* (2013.01); *A61B 8/0883* (2013.01); *A61B 8/5207* (2013.01); *A61B 8/5223* (2013.01); *A61B 8/5269* (2013.01); *G01S 7/52026* (2013.01); *G01S 7/52077* (2013.01);

(Continued)

(58) Field of Classification Search
USPC ................................ 382/128, 130, 131, 263
See application file for complete search history.

(56) References Cited

U.S. PATENT DOCUMENTS 5,479,926 A    1/1996   Ustuner et al.
5,671,744 A    9/1997   Abe et al.
(Continued)

FOREIGN PATENT DOCUMENTS

CN    1695561 A    11/2005
JP    08-107896 A   4/1996
(Continued)

OTHER PUBLICATIONS

English translated of JP2009-005737, Jan. 15, 2009.*
(Continued)

*Primary Examiner* — Duy M Dang
(74) *Attorney, Agent, or Firm* — Westerman, Hattori, Daniels & Adrian, LLP

(57) ABSTRACT

In ultrasound images, there are many stationary echoes in the region superficial to the deep region comprising the heart. In the present invention, a HPF processing unit (20) filters frame data by applying a high pass filter, the characteristics of which have been set according to the depth in the frame, on the frame data at said depth. The high pass filter can be achieved, for example, with a digital filter and the characteristics of the high pass filter are adjusted by the filter-setting unit (22) setting the filter coefficient of said digital filter. That is to say, the filter coefficient in the HPF processing unit (20) is controlled by the filter-setting unit (22) so that the deeper the region, the higher the offset level is set.

12 Claims, 10 Drawing Sheets

(52) U.S. Cl.
CPC ............... *G06T 2207/10016* (2013.01); *G06T 2207/10132* (2013.01); *G06T 2207/20024* (2013.01)

(56) References Cited

U.S. PATENT DOCUMENTS

| | | |
|---|---|---|
| 2005/0256404 A1 | 11/2005 | Sato |
| 2007/0239015 A1 | 10/2007 | Sato |
| 2009/0209861 A1 | 8/2009 | Nishigaki et al. |

FOREIGN PATENT DOCUMENTS

| | | |
|---|---|---|
| JP | 2000-139909 A | 5/2000 |
| JP | 2000-166924 A | 6/2000 |
| JP | 2000-316846 A | 11/2000 |
| JP | 2005-288021 A | 10/2005 |
| JP | 2006-231069 A | 9/2006 |
| JP | 2006-271557 A | 10/2006 |
| JP | 2007-222390 A | 9/2007 |
| JP | 2009-005737 A | 1/2009 |
| JP | 2013-180035 A | 9/2013 |
| WO | 2006/088094 A1 | 8/2006 |

OTHER PUBLICATIONS

International Search Report dated Mar. 26, 2013, issued in corresponding application No. PCT/JP2013/054015.

Written Opinion dated Mar. 26, 2013, issued in corresponding application No. PCT/JP2013/054015 (3 pages).

Notice of Grounds for Rejection dated Mar. 19, 2013, issued in corresponding application No. JP2012-045280; w/English translation (4 pages).

Notice of Grounds for Rejection dated Feb. 25, 2014, issued in corresponding application No. JP2012-045282; w/English translation (4 pages).

Notification of Transmittal of Translation of the International Preliminary Report on Patentability (Forms PCT/IB/326) of International Application No. PCT/JP2013/054015 mailed Sep. 2, 2014 with Forms PCT/IB1373, PCT/IB/338 and PCT/ISA1237, with English Translation.

Office Action dated Jul. 28, 2015, issued in counterpart Chinese Patent Application No. 2013800120736, with English translation (15 pages).

* cited by examiner

<A> 3-TAP FIR FILTER

<B> 2-TAP FIR FILTER

DIAGNOSTIC ULTRASOUND APPARATUS

TECHNICAL FIELD

The present invention relates to an ultrasonic diagnostic apparatus, and more particularly to a technology of improving image quality of an ultrasonic image.

BACKGROUND ART

Ultrasonic diagnostic apparatuses, which are being widely used for diagnosis of organs, blood vessels, and fetuses, have played a significant role in diagnosis of heart conditions, for example. Use of an ultrasonic diagnostic apparatus enables observation of a beating heart, for example, in an ultrasonic moving image.

During ultrasonic diagnosis of heart conditions, fixed echoes (stationary echoes) are generated in an ultrasonic image due to the chest wall, ribs, pericardium, and so on, that are present on a superficial side (toward the probe) with respect to the heart. These stationary echoes cause deterioration of the quality of an ultrasonic image in ultrasonic diagnosis targeted on the heart. There have therefore conventionally been proposed methods of reducing these stationary echoes.

Patent Document 1, for example, proposes technology of applying a high-pass filter (HPF) to frame data obtained by transmitting and receiving ultrasound, along an arrangement direction of a plurality of frames, i.e. applying HPF processing between frames (inter-frame HPF processing), to thereby reduce stationary echoes whose fluctuations concerning the arrangement direction (time direction) of the plurality of frames are smaller than those of the heart.

With the simple inter-frame HPF processing, however, as it is difficult to completely maintain echoes from the heart with only the stationary echoes being completely removed, residual stationary echoes are partially generated, or loss of echoes from the heart occurs, resulting in generation of flicker within the moving image. Further, processing corresponding to weighted summation between a plurality of frames in the inter-frame HPF processing causes a problem that a heart valve or the like which moves at a high speed appears double or triple in the moving image, and also a problem that the borderline of the heart (cardiac muscle) becomes blurred.

Patent Document 2, for example, proposes technology of further performing inter-frame LPF (low-pass filter) processing after the inter-frame HPF processing in order to reduce the flicker described above. In other words, smoothing (flattening) between the frames is performed by the LPF processing to thereby reduce the flicker. This technology, however, suffers from a further problem that the inter-frame LPF processing, when simply performed for a whole image, makes the whole image blurred.

Patent Document 3, for example, proposes technology of increasing the weight of frame data after HPF processing in a superficial region in which a large number of stationary echoes are present and increasing the weight of frame data before the HPF processing in a deep region in which the heart exists, so that weighted summation is applied to frame data before and after the HPF processing, in order to suppress the flicker and blurring described above. With this technology, the stationary echoes are reduced in the superficial region while flicker and blurring relating to the heart are suppressed in the deep region. However, this technology also causes a problem with respect to circuit scale, such as a problem that a circuit structure for applying weighted summation is necessary, for example.

PRIOR ART DOCUMENTS

Patent Documents

Patent Document 1: JP H8-107896 A
Patent Document 2: JP 2000-139909 A
Patent Document 3: JP 2005-288021 A

DISCLOSURE OF THE INVENTION

Technical Problems

In view of the background art described above, the present inventor has for many years studied and developed technology of improving the quality of an ultrasonic image including a moving subject to be diagnosed such as a heart, for example, and has, in particular, paid attention to filter processing along the arrangement direction of a plurality of frames.

The present invention has been made in the process of such study and development and is aimed at realizing an improved technology related to filter processing along the arrangement direction of a plurality of frames.

Solution to Problems

In order to achieve the above object, there is provided an ultrasonic diagnostic apparatus, including a probe that transmits and receives ultrasound; a transmitter/receiver section that controls the probe to thereby obtain a reception signal of ultrasound; a filter processing section that applies filter processing to frame data obtained based on the reception signal of ultrasound along an arrangement direction of a plurality of frames; and an image forming section that forms an ultrasonic image based on the frame data having been subjected to the filter processing, wherein the filter processing section applies a high-pass filter, having an offset level set in accordance with a depth within a frame, to frame data at the depth, thereby performing the filter processing.

In the above ultrasonic diagnostic apparatus, a high-pass filter having an offset level set in accordance with a depth within a frame is applied to frame data at the corresponding depth. The offset of a high-pass filter refers to boosting gain characteristics of the high-pass filter, and the offset level is defined by a gain value of the filter at the lower limit (e.g., 0 Hz) of the frequency band which is a target of processing by the high-pass filter, for example.

The offset level can be adjusted to a desired level relatively easily in a digital filter, for example, by changing a filter coefficient and so on. Therefore, according to the ultrasonic diagnostic apparatus described above, in order to improve the quality of an ultrasonic image by filter processing along the arrangement direction of a plurality of frames, it is possible to adjust the characteristics of the high-pass filter with relative ease in accordance with the depth.

In a preferred specific example, the filter processing section subjects frame data of a deep region including a moving subject to be diagnosed to a high-pass filter having an offset level set to a higher level than frame data of a superficial region.

In a preferred specific example, the filter processing section applies a high-pass filter having an offset level set to a higher level as the depth within a frame becomes greater, and having characteristics closer to characteristics of an all-pass filter as the depth within a frame becomes greater.

In a preferred specific example, the ultrasonic diagnostic apparatus further includes a post-processing section that applies a low-pass filter or a median filter to the frame data processed by the filter processing section along the arrangement direction of the plurality of frames.

In a preferred specific example, the post-processing section, in a case of applying a low-pass filter, applies a low-pass filter, having an offset level set in accordance with a depth within a frame, to frame data at the depth.

In a preferred specific example, the post-processing section, in a case of applying a median filter, applies a median filter exclusively to frame data of a superficial region which is different from a deep region including a moving subject to be diagnosed.

In a preferred specific example, the ultrasonic diagnostic apparatus further includes a determination section that confirms a change of the frame data processed by the filter processing section at each of locations within a frame along the arrangement direction of the plurality of frames, to thereby determine whether or not the processing performed by the post-processing section is necessary at a corresponding location.

In a preferred specific example, the filter processing section applies a digital high-pass filter, having a filter coefficient set in accordance with a frame rate of frame data and a depth of frame data within a frame, to the frame data.

Advantageous Effects of Invention

According to the present invention, an improved technology related to filter processing along the arrangement direction of a plurality of frames is realized. For example, in accordance with a preferred aspect of the present invention, it is possible to adjust the characteristics of a high-pass filter with relative ease in accordance with the depth. Further, in accordance with another preferred aspect of the present invention, application of a digital high-pass filter having a filter coefficient set in accordance with a frame rate can suppress fluctuations of processing results of the digital high-pass filter in accordance with a frame rate.

BEST MODE FOR CARRYING OUT THE INVENTION

Figure 1:
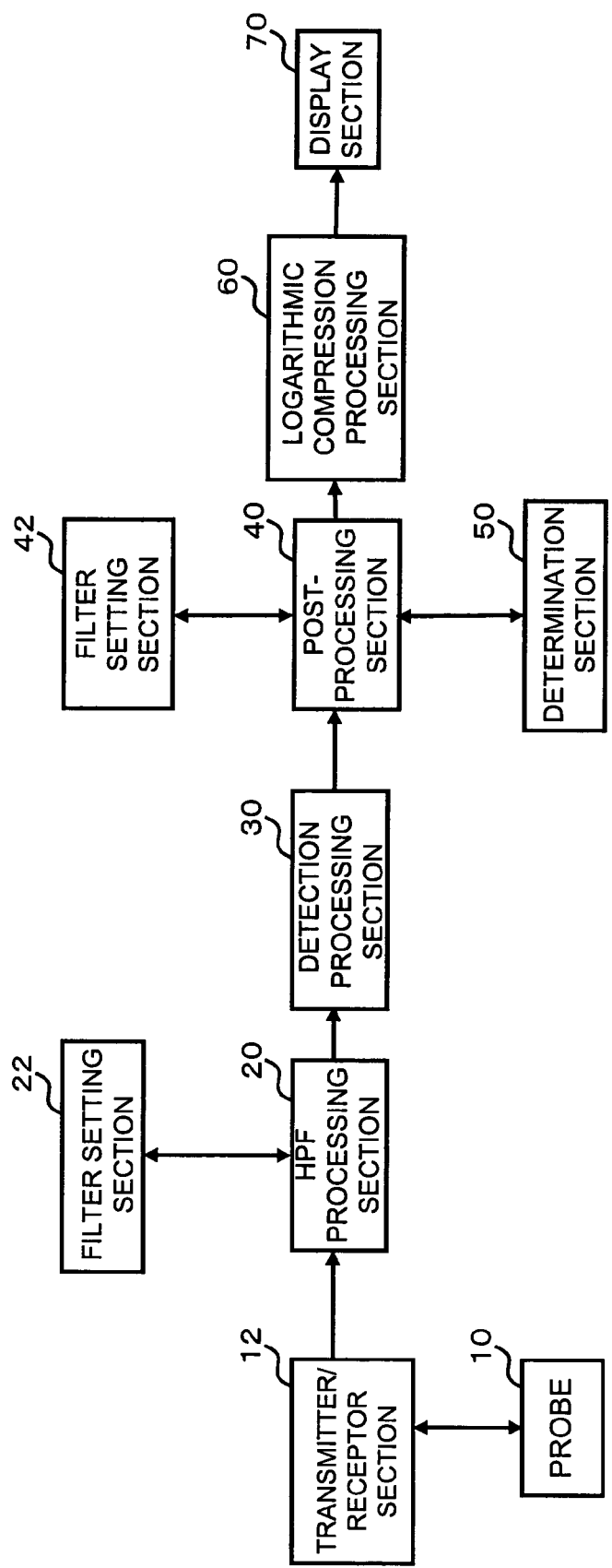
FIG. 1 Diagram illustrating an overall structure of a preferable ultrasonic diagnostic apparatus in an embodiment of the present invention FIG. 2 Diagram illustrating a specific example of a digital filter.

FIG. 1 is a diagram illustrating an overall structure of an ultrasonic diagnostic apparatus which is preferable in an embodiment of the present invention (which will be hereinafter referred to as the present ultrasonic diagnostic apparatus). A probe 10 transmits ultrasound to a diagnostic region including a tissue to be diagnosed, and receives ultrasound reflected from the diagnostic region. The probe 10 includes a plurality of transducer elements for transmitting and receiving ultrasound, and the plurality of transducer elements are transmission-controlled by a transmitter/receiver section 12, which forms a transmission beam. The plurality of transducer elements also receive ultrasound reflected from the diagnostic region. A signal obtained by reception of the ultrasound is output to the transmitter/receiver section 12, which then forms a reception beam.

The transmitter/receiver section 12 outputs transmission signals corresponding to the plurality of transducer elements, respectively, of the probe 10, thereby forming a transmission beam of ultrasound and scanning the transmission beam. Further, the transmitter/receiver section 12 applies phase alignment and summation processing and other processing to reception signals obtained from the respective plurality of transducer elements of the probe 10, thereby forming a reception beam corresponding to the transmission beam which is scanned, and outputting echo data (reception signal) obtained along the reception beam.

The transmitter/receiver section 12 scans ultrasonic beams (a transmission beam and a corresponding reception beam) within a two-dimensional plane and collects echo data, thereby obtaining frame data forming a frame corresponding to the two-dimensional plane. The transmitter/receiver section 12 repeats scanning of the ultrasonic beams within the two-dimensional plane to thereby obtain frame data for a plurality of frames. The frame data thus obtained is stored in a memory, for example, and is read from the memory for processing by a HPF processing section 20 on the downstream side, for example.

The present ultrasonic diagnostic apparatus is suitable for diagnosis of a moving tissue such as the heart, for example, and is provided with a function to improve the quality of an ultrasonic image including a subject to be diagnosed, such as the heart. More specifically, the present ultrasonic diagnostic apparatus reduces fixed echoes (stationary echoes) associated with the chest wall, ribs, pericardium, and so on, that are present on a superficial side (toward the probe 10) with respect to the heart, thereby improving the quality of the ultrasonic image.

The HPF (high-pass filter) processing section 20 performs filter processing of the frame data obtained for the plurality of frames in order to reduce the stationary echo. The HPF processing section 20 applies a high-pass filter along the arrangement direction of the plurality of frames, i.e. applies inter-frame HPF processing, to the frame data, thereby reducing stationary echoes whose fluctuations in the arrangement direction of the plurality of frames (time direction) are smaller than those of the heart.

In an ultrasonic image, there are more stationary echoes present in a superficial region than in a deep region containing heart. Accordingly, the HPF processing section 20 performs filter processing by applying a high-pass filter, having characteristics set in accordance with a depth in a frame, to frame data at the corresponding depth. The high-pass filter can be implemented by a digital filter, for example, and a filter setting section 22 sets a filter coefficient and so on of the digital filter to thereby adjust the characteristics of the high-pass filter.

Figure 2:
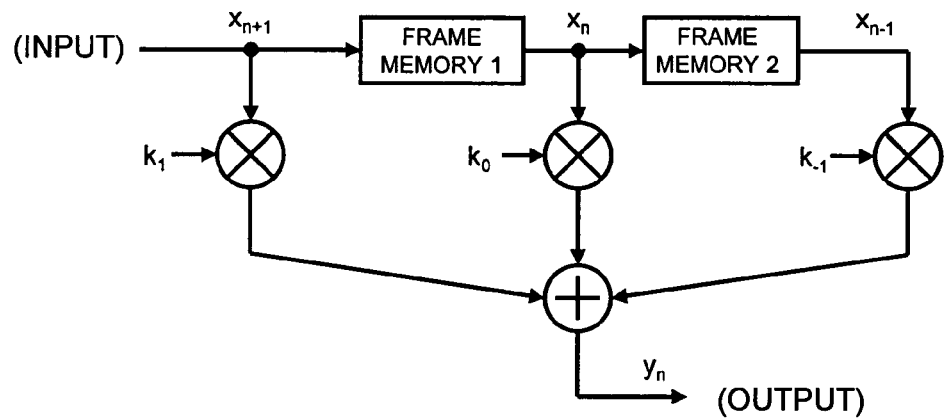
Figure 2:
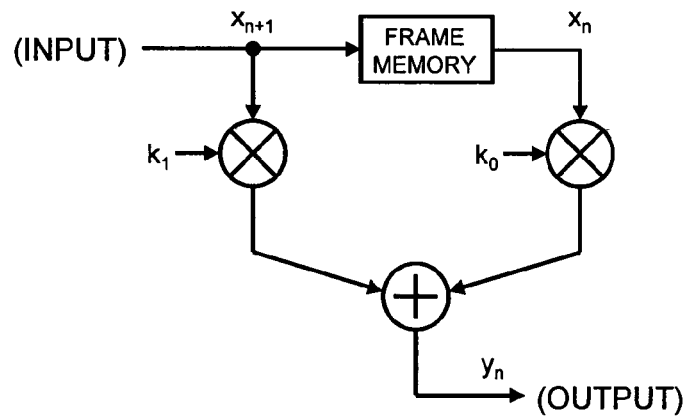

FIG. 2 is a diagram illustrating a specific example digital filter. The frame data is subjected to filter processing along the arrangement direction of the plurality of frames. More specifically, concerning frame data at a certain location (coordinates) within a frame, frame data at the same location is sequentially subjected to filter processing through the plurality of frames.

FIG. 2<A> illustrates a FIR filter with 3 taps (3-tap FIR filter). The frame data of the plurality of frames is sequentially input to this 3-tap FIR filter. In FIG. 2<A>, $x_{n-1}$, $x_n$, and $x_{n+1}$ denote frame data at the same location (coordinates) within the frame, that can be obtained from three consecutive frames.

Frame data of one frame input to the 3-tap FIR filter is stored in a frame memory 1. Then, when frame data of a new one frame is input, the frame data stored in the frame memory 1 is now stored in a frame memory 2 in the following stage, and the newly input frame data of one frame is stored in the frame memory 1 in the previous stage. In this manner, each time frame data of new one frame is input, frame data stored in the frame memory 1 in the previous stage is sequentially shifted to the frame memory 2 in the following stage. In FIG. 2<A>, $x_n$ denotes frame data of a noted frame; $x_{n-1}$ denotes frame data obtained from the one frame previous to the frame of the frame data $x_n$, and $x_{n+1}$ denotes frame data obtained from one frame after the frame of the frame data $x_n$.

The 3-tap FIR filter multiplies each of the three frame data obtained from the three consecutive frames by a filter coefficient and further adds the three data items after multiplication together. More specifically, in FIG. 2<A>, each of the frame data $x_{n-1}$, $x_n$, and $x_{n+1}$ is multiplied by filter coefficients $k_{-1}$, $k_0$, and $k_1$, respectively, and the resulting three data items after the multiplication are further added to output the result of filter processing for the noted frame $y_n = k_{-1}x_{n-1} + k_0 x_n + k_1 x_{n+1}$.

FIG. 2<B> illustrates a FIR filter with 2 taps (2-tap FIR filter). In the case of a 2-tap FIR filter, similar to the case of the 3-tap FIR filter, frame data concerning a plurality of frames is sequentially input and frame data of one frame is stored in a frame memory. In FIG. 2<B>, $x_n$ denotes frame data of a noted frame, and $x_n$ and $x_{n+1}$ denote frame data at the same location within the frame, that can be obtained from two consecutive frames.

In the case of the 2-tap FIR filter, as in the case of the 3-tap FIR filter, each of the frame data $x_n$ and $x_{n+1}$ is multiplied by each of filter coefficients $k_0$ and $k_1$ and the resulting two data items after the multiplication are further added to output the result of filter processing concerning the noted frame $y_n = k_0 x_n + k_1 x_{n+1}$.

With the present ultrasonic diagnostic apparatus, for example, a high-pass filter is realized with the 3-tap FIR filter or 2-tap FIR filter illustrated in FIG. 2, and the characteristics of the high-pass filter are adjusted by adjusting the filter coefficient. While FIG. 2 illustrates 2-tap and 3-tap FIR filters as specific digital filter examples, a filter with 4 or more taps may also be used. Also, an IIR filter may be used in place of a FIR filter.

Figure 3:
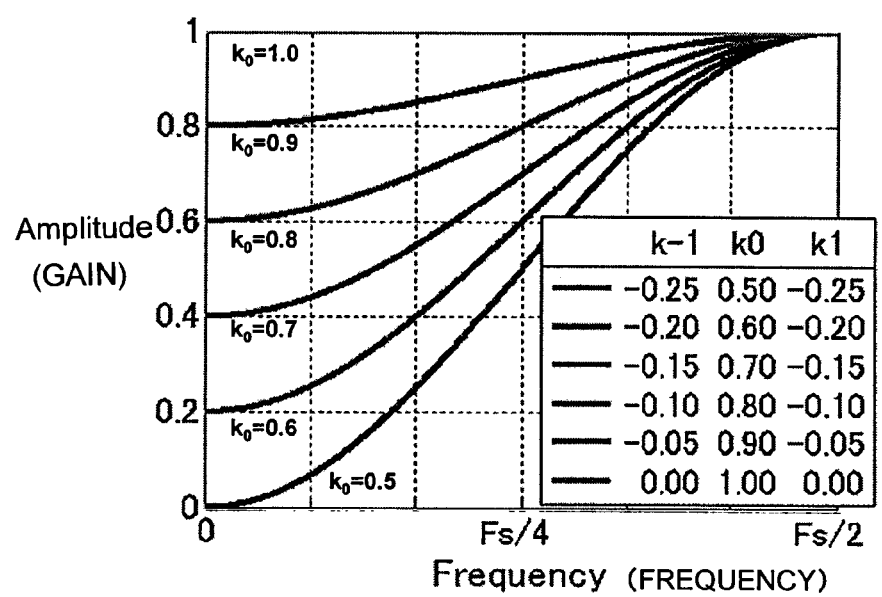
FIG. 3 Diagram illustrating frequency characteristics of a HPF formed of a 3-tap FIR filter.

Concerning the 3-tap FIR filter illustrated in FIG. 2, if the filter coefficient is set that satisfies the following conditions (1-1) and (1-2) in which filter coefficients are symmetrical ($k_{-1} = k_1$), the gain characteristics increase monotonically with respect to the frequency, and the gain at the highest frequency is 0 [dB], a high-pass filter (HPF) exhibiting the characteristics illustrated in FIG. 3 is obtained.

[Expression 1]

$$-0.25 \le k_1 \le 0, 0.5 \le k_0 \le 1 \tag{1-1}$$

$$|k_{-1}| + |k_0| + |k_1| = 1 \tag{1-2}$$

FIG. 3 illustrates frequency characteristics of a HPF formed of the 3-tap FIR filter (FIG. 2). In FIG. 3, the horizontal axis shows the frequency, in which Fs denotes a frame rate, i.e., a sampling frequency of frame data. The vertical axis shows gain of the filter. In FIG. 3, $k_{-1}$, $k_0$, and $k_1$ are filter coefficients of the 3-tap FIR filter (FIG. 2).

According to the frequency characteristics illustrated in FIG. 3, the offset level of the HPF changes in accordance with the filter coefficient. The offset of the HPF refers to boosting the gain characteristics of the HPF. In FIG. 3, the gain value of the filter at 0 Hz which is the lower limit of the frequency band to be processed with the HPF is defined as the offset level.

In FIG. 3, when the filter coefficient for the center tap $k_0$ is 0.5, the offset level is minimum, 0, and the suppression efficiency on the low frequency side, i.e. the effect of suppressing stationary echoes, is the greatest. As the filter coefficient $k_0$ increases from 0.5, the offset level also increases and the suppression effect of stationary echoes gradually decreases. Then, the offset level is the maximum, 1, when the filter coefficient $k_0$ is 1.0, and no suppression effect on the lower frequency side, i.e. no suppression effect of stationary echoes, can be obtained, showing filter characteristics of an all-pass filter in which an input signal is output as it is.

According to the present ultrasonic diagnostic apparatus, the offset level of the HPF is set in accordance with the depth of the frame data within a frame. Specifically, the filter setting section 22 in FIG. 1 controls the filter coefficient $k_0$ in the HPF processing section 20 such that the greater the depth, the higher the offset level set.

Figure 4:
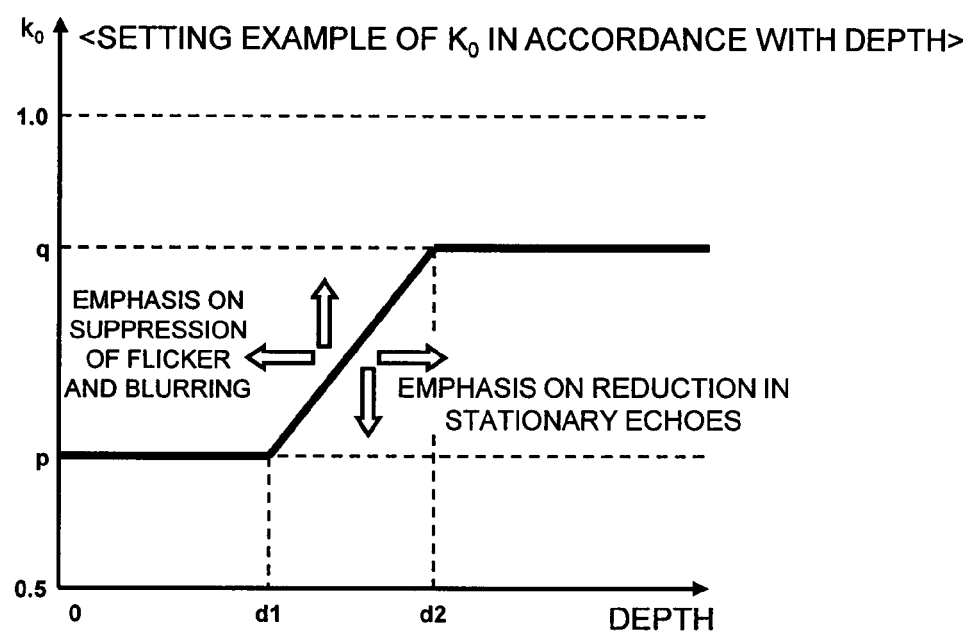
FIG. 4 View illustrating an example setting of a filter coefficient $k_0$ in accordance with a depth.

FIG. 4 illustrates a setting example of the filter coefficient $k_0$ in accordance with the depth. In FIG. 4, the horizontal axis shows the depth and the vertical axis shows the value of the filter coefficient $k_0$. The depth refers to a depth of frame data to be processed by the filter within a frame.

In the setting example illustrated in FIG. 4, in the superficial portion from the depth of 0 (proximate the probe 10) to the depth of d1, the value of the filter coefficient $k_0$ is set to p ($0.5 \le p < 1.0$). As the depth increases from d1 to d2, the value of the filter coefficient $k_0$ is increased, and in the depth portion at the depth d2 or a greater depth, the value of the filter coefficient $k_0$ is set to q ($p < q \le 1.0$). The value of the filter coefficient $k_0$ may be smoothly changed at the depth d1 and in the vicinity thereof and at the depth d2 and in the vicinity thereof. Further, the value of the filter coefficient $k_0$ may be varied as necessary in the superficial portion from the depth of 0 to the depth of d1 and also in the deep portion at the depth d2 and greater depths. It is also possible to adjust the positions of the depth d1 and the depth d2 as appropriate, to thereby make the change of the filter coefficient $k_0$ in accordance with the depth steep or moderate.

Further, if it is desired to place importance on the effect of reducing the stationary echoes in the superficial region, the characteristics of the filter coefficient $k_0$ illustrated in FIG. 4 can be shifted to the direction of greater depth as a whole or in the direction of smaller $k_0$ value as a whole. Of course, the shifts in both directions can be performed together. Also, if it is desired to place importance on the effect of suppressing flicker and blurring, the characteristics of the filter coefficient $k_0$ illustrated in FIG. 4 can be shifted to the direction of smaller depth as a whole or in the direction of greater $k_0$ value as a whole. Of course, the shifts in both directions can be performed together.

Figure 5:
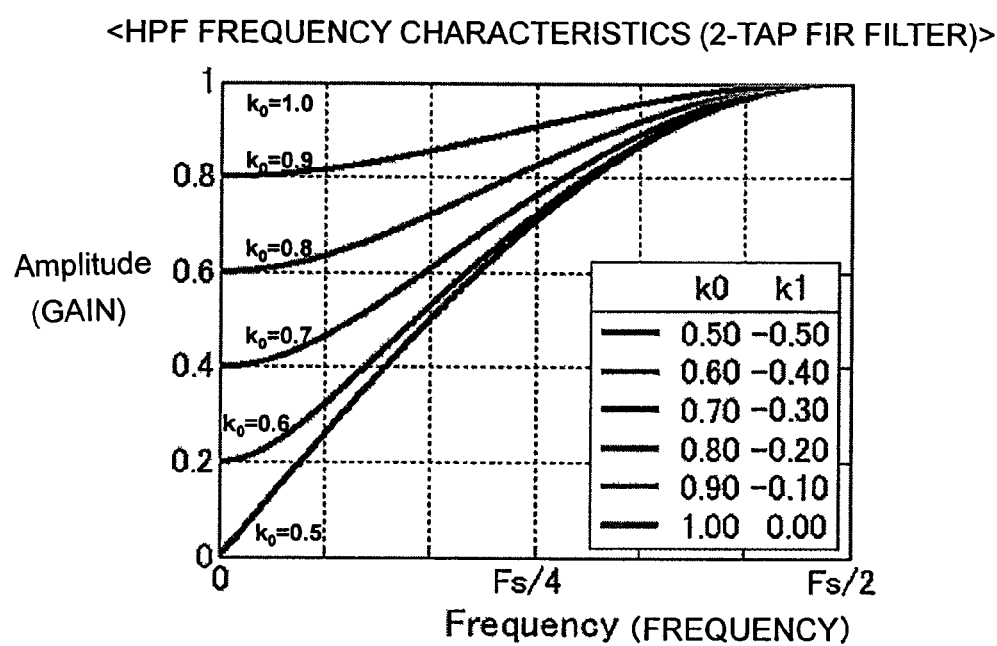
FIG. 5 Diagram illustrating frequency characteristics of a HPF formed of a 2-tap FIR filter.

If a 2-tap FIR filter is used in place of a 3-tap FIR filter, the circuit configuration or the like can be further simplified. For example, concerning the 2-tap FIR filter illustrated in FIG. 2, if the filter coefficient is set that satisfies the following conditions (2-1) and (2-2) in which the gain characteristics increase monotonically with respect to the frequency, and the gain at the highest frequency is 0 [dB], a high-pass filter (HPF) exhibiting the characteristics illustrated in FIG. 5 is obtained.

[Expression 2]

$$0.5 \leq k_0 \leq 1, 0.5 \leq k_1 \leq 0 \quad (2\text{-}1)$$

$$|k_0| + |k_1| = 1 \quad (2\text{-}2)$$

FIG. 5 illustrates frequency characteristics of a HPF formed of the 2-tap FIR filter (FIG. 2). As in the case illustrated in FIG. 3, in FIG. 5, the horizontal axis similarly shows the frequency, in which Fs denotes a frame rate, i.e., a sampling frequency of frame data. The vertical axis similarly shows the gain of the filter. In FIG. 5, $k_0$ and $k_1$ are filter coefficients of the 2-tap FIR filter (FIG. 2). In the frequency characteristics illustrated in FIG. 5, as in the case in FIG. 3, the offset level of the HPF varies in accordance with the filter coefficient.

More specifically, assuming that the gain value of the filter at 0 Hz, which is the lower limit of the frequency band to be processed with the HPF, is defined as the offset level, in FIG. 5, as in FIG. 4, when the filter coefficient $k_0$ is 0.5, the offset level is minimum, 0, and the suppression efficiency on the low frequency side, i.e. the effect of suppressing stationary echoes, is the greatest. As the filter coefficient $k_0$ increases from 0.5, the offset level also increases and the suppression effect of stationary echoes gradually decreases. Then, the offset level is the maximum, 1, when the filter coefficient $k_0$ is 1.0, and no suppression effect on the lower frequency side, i.e. no suppression effect of stationary echoes, can be obtained, showing filter characteristics of an all-pass filter.

In the case of a 2-tap FIR filter, as in the case of a 3-tap FIR filter, the offset level of the HPF is set in accordance with the depth of the frame data within a frame. Specifically, the filter setting section 22 in FIG. 1 controls the filter coefficient $k_0$ such that the greater the depth, the higher the offset level set. For this control, the setting example of the filter coefficient $k_0$, which has been described with the use of FIG. 4, can be applied.

With the use of the high-pass filter which has been described with reference to FIGS. 2 to 5, it is possible to achieve both reduction in the stationary echoes and suppression of flicker and blurring simultaneously, with a relatively simple structure, i.e. without the need to provide a complicated circuit structure (see Patent Document 3, for example) such as for weighted summation processing.

Referring back to FIG. 1, the frame data of a plurality of frames having been subjected to the inter-frame HPF processing in the HPF processing section 20 is first subjected to detection processing in a detection processing section 30 and then transmitted to a post-processing section 40. In the detection processing section 30, known detection processing is executed.

While reduction of the stationary echoes and suppression of flicker and blurring in an image has been already realized by the processing in the HPF processing section 20, with the present ultrasonic diagnostic apparatus, it is possible to further suppress the flicker in an image by the post-processing section 40. The post-processing section 40 applies a low-pass filter or a median filter to the frame data, along the arrangement direction of the plurality of frames.

Figure 6:
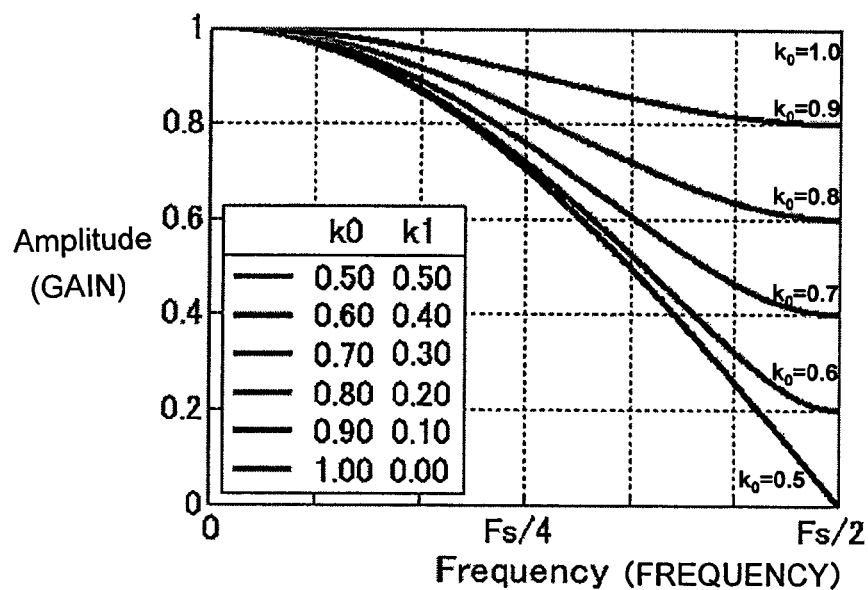
FIG. 6 Diagram illustrating frequency characteristics of a LPF formed of a 2-tap FIR filter.

If the post-processing section 40 uses a low-pass filter (LPF), the low-pass filter can be implemented by the 3-tap FIR filter or the 2-tap FIR filter illustrated in FIG. 2. Of course, a filter with 4 or more taps may be used or an IIR filter may be used in place of an FIR filter. For example, concerning the 2-tap FIR filter illustrated in FIG. 2, if the filter coefficient is set that satisfies the following conditions (3-1) and (3-2) in which the gain characteristics decrease monotonically with respect to the frequency, and the gain of DC components (frequency 0 Hz components) is 0 [dB], a low pass filter (LPF) exhibiting the characteristics illustrated in FIG. 6 is obtained.

[Expression 3]

$$0.5 \leq k_0 \leq 1 \quad (3\text{-}1)$$

$$k_0 + k_1 = 1 \quad (3\text{-}2)$$

FIG. 6 illustrates frequency characteristics of a LPF formed of the 2-tap FIR filter (FIG. 2). In FIG. 6, the horizontal axis shows the frequency, in which Fs denotes a frame rate, i.e., a sampling frequency of frame data. The vertical axis shows the gain of the filter. In FIG. 6, $k_0$ and $k_1$ are filter coefficients of the 2-tap FIR filter (FIG. 2).

In the frequency characteristics illustrated in FIG. 6, the offset level changes in accordance with the filter coefficient. The offset of LPF refers to boosting the gain characteristics of the LPF. In FIG. 6, the gain value of a filter at Fs/2 Hz, which is the upper limit of the frequency band to be processed with the LPF, i.e. at a frequency which is a half the sampling frequency, is defined as the offset level.

In FIG. 6, when the filter coefficient $k_0$ is 0.5, the offset level is minimum, 0, and the suppression efficiency on the high frequency side, i.e. the smoothing effect, is the greatest. With the increase in the smoothing effect in the arrangement direction of a plurality of frames, the suppression effect of flicker is also increased. Then, as the filter coefficient $k_0$ increases from 0.5, the offset level increases and the smoothing effect gradually decreases. Then, when the filter coefficient $k_0$ is 1.0, the offset level is the maximum, 1, and no suppression effect on the higher frequency side, i.e. no smoothing effect, can be obtained, showing filter characteristics of an all-pass filter in which an input signal is output as it is.

In the present ultrasonic diagnostic apparatus, the offset level of the LPF is set in accordance with the depth of the frame data within a frame. Specifically, a filter setting section 42 in FIG. 1 controls the filter coefficient $k_0$ in the post-processing section 40 such that the greater the depth, the higher the offset level set. For this control, the setting example of the filter coefficient $k_0$, which has been described with the use of FIG. 4, can be applied.

Figure 7:
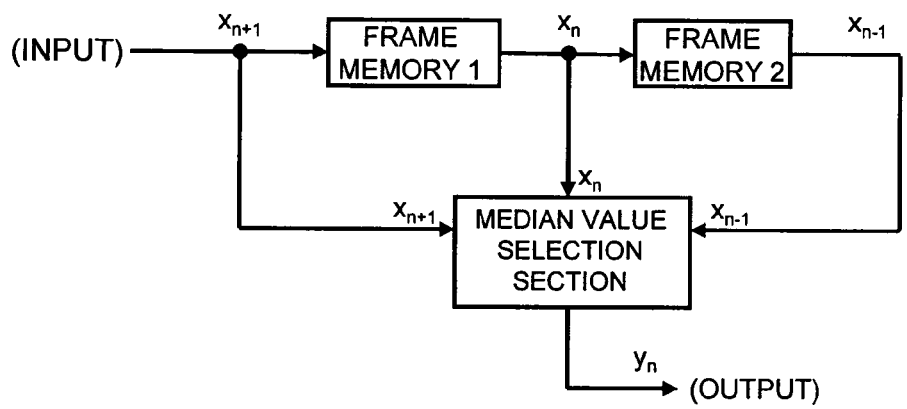
FIG. 7 Diagram illustrating a specific example of a median filter.

If the post-processing section 40 uses a median filter, a median filter having a structure illustrated in FIG. 7, for example, is used. FIG. 7 illustrates a specific example median filter. Frame data of a plurality of frames is sequentially input to this median filter. In FIG. 7, $x_n$ is frame data of a noted frame. Further, $x_{n-1}$, $x_n$, and $x_{n+1}$ denote frame data at the same location (coordinates) within the frame, that can be obtained from three consecutive frames.

Frame data of one frame input to the median filter is stored in a frame memory 1. Then, when frame data of a new one frame is input, the frame data stored in the frame memory 1 is now stored in a frame memory 2 in the following stage, and the newly input frame data of one frame is stored in the frame memory 1 in the previous stage. In this manner, each time frame data of new one frame is input, frame data stored in the frame memory 1 in the previous stage is sequentially shifted to the frame memory 2 in the following stage. In FIG. 7, $x_{n-1}$ denotes frame data obtained from the one previous frame to the frame of the frame data $x_n$, and $x_{n+1}$ denotes frame data obtained from one frame after the frame of the frame data $x_n$.

The median filter selects and outputs a median value of the three frame data obtained from three consecutive frames. More specifically, in FIG. 7, the median filter selects data corresponding to a median value of $x_{n-1}$, $x_n$, and $x_{n+1}$, and outputs the selected data as a processing result $y_n$ in the noted frame.

With the median filter, it is possible to suppress flicker while suppressing blurring in an image. Here, it is more desirable to apply a median filter locally to a superficial portion within the frame than to apply a median filter to a whole image. More specifically, it is desirable to give consideration to prevent generation of blurring in n image of a heart valve and the like by applying no median filter to a deep region in which the heart exists. For example, it is possible to set a threshold value of the depth and prevent application of a median filter to the frame data at a location which is deeper than the threshold value.

Further, a determination section 50 in FIG. 1 may determine whether or not the processing in the post-processing section 40 is necessary. In this case, concerning the frame data obtained via the detection processing section 30 after having been processed in the HPF processing section 20, the determination section 50 confirms a change of the frame data in the arrangement direction of a plurality of frames at each location within the frame, thereby determining whether or not the processing in the post-processing section 40 is necessary at that location.

Figure 8:
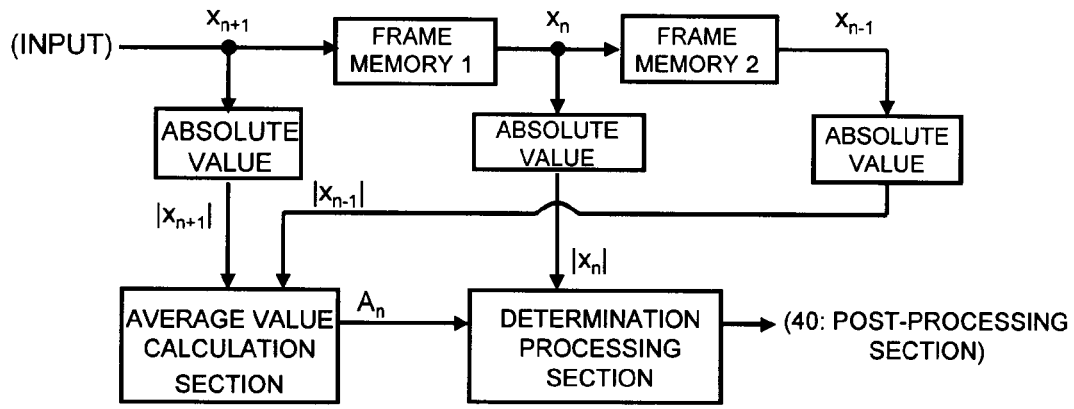
FIG. 8 Diagram illustrating a specific example of a determination section.

FIG. 8 illustrates a specific example of the determination section 50. Frame data of a plurality of frames is sequentially input to the determination section 50. In FIG. 8, $x_{n-1}$, $x_n$, and $x_{n+1}$ denote frame data at the same location (coordinates) within the frame, that can be obtained from three consecutive frames.

Frame data of one frame input to the determination section 50 is stored in a frame memory 1. Then, when frame data of a new one frame is input, the frame data stored in the frame memory 1 is now stored in a frame memory 2 in the following stage, and the newly input frame data of one frame is stored in the frame memory 1 in the previous stage. In this manner, each time frame data of new one frame is input, frame data stored in the frame memory 1 in the previous stage is sequentially shifted to the frame memory 2 in the following stage. In FIG. 8, $x_n$ is frame data of a noted frame, $x_{n-1}$ denotes frame data obtained from the one previous frame to the frame of the frame data $x_n$, and $x_{n+1}$ denotes frame data obtained from one frame after the frame of the frame data $x_n$.

An average value calculation section calculates an average value $A_n$ of absolute values of the frame data before and after the noted frame using the following equation, wherein M denotes the number of frames before or after the noted frame, which is M=1 in the specific example in FIG. 8.

[Expression 4]

$$A_n = \frac{1}{2M} \sum_{m=1}^{M} (|x_{n-m}| + |x_{n+m}|) \quad (4)$$

A determination processing section compares an absolute value for the frame data of the noted frame with the average value $A_n$ calculated in the average value calculation section, and determines, for the frame data of the noted frame, whether or not processing to suppress flicker is necessary, based on the conditions in the following expressions.

[Expression 5]

$$||x_n|-A_n| \geq T_H \quad (5\text{-}1)$$

$$||x_n|-A_n|/A_n \geq T_H \quad (5\text{-}2)$$

In the conditions (5-1) and (5-2), $T_H$ is a threshold value used for determining flicker. If the condition (5-1) is satisfied, for example, it is determined that flicker suppression processing is necessary for the frame data $x_n$ of the noted frame. Further, the condition (5-2) which is normalized by the average value $A_n$ may be used in place of the condition (5-1).

Referring back to FIG. 1, the post-processing section 40 executes flickes suppression processing for the frame data of the noted frame for which it is determined that flicker suppression processing is necessary in the determination section 50, and does not execute flicker suppression processing for the frame data of the noted frame for which it is determined that flicker suppression processing is not necessary. When the flicker suppression processing is performed, the LPF which has been described with reference to FIG. 6 or the median filter which has been described with reference to FIG. 7, for example, is applied. Further, the post-processing section 40 in FIG. 1 may output the average value $A_n$ obtained by the expression (4), as a result of the flicker suppression processing for the frame data of the noted frame.

A logarithmic compression processing section 60 executes known logarithmic compression processing for the frame data of a plurality of frames obtained from the post-processing section 40. The frame data of a plurality of frames having been subjected to the logarithmic compression processing is then transmitted to a display section 70, and an ultrasonic image, which is a moving image expressing a beating heart, for example, is displayed on the display section 70. The post-processing section 40 may be provided downstream of the logarithmic compression processing section 60.

As described above, according to the present ultrasonic diagnostic apparatus, it is possible to achieve reduction of the stationary echoes and suppression of flicker and blurring of an image in the HPF processing section 20 and further suppress image flicker in the post-processing section 40. When performing this processing, the HPF processing section 20 uses a high-pass filter whose characteristics are set in accordance with the depth in a frame and the post-processing section 40 uses a low-pass filter whose characteristics are set in accordance with the depth in a frame. In other words, the characteristics of the high-pass filter and the low-pass filter are adjusted in accordance with the depth in a frame.

When the high-pass filter and the low-pass filter are implemented by a digital filter, while the filter characteristics of a digital filter are determined by adjusting setting of a filter coefficient and so on, the characteristics of a digital filter also depend on the sampling frequency of data to be processed. In filter processing along the arrangement direction of a plurality of frames, the sampling frequency of frame data to be processed changes depending on the frame rate. Accordingly, when a digital filter is used in filter processing along the arrangement direction of a plurality of frames, it is necessary to take into consideration the dependency of the characteristics of the digital filter on the frame rate.

The present ultrasonic diagnostic apparatus applies a digital filter having a filter coefficient set in accordance with a frame rate, to thereby suppress fluctuations of the results of filter processing in accordance with the frame rate.

Figure 9:
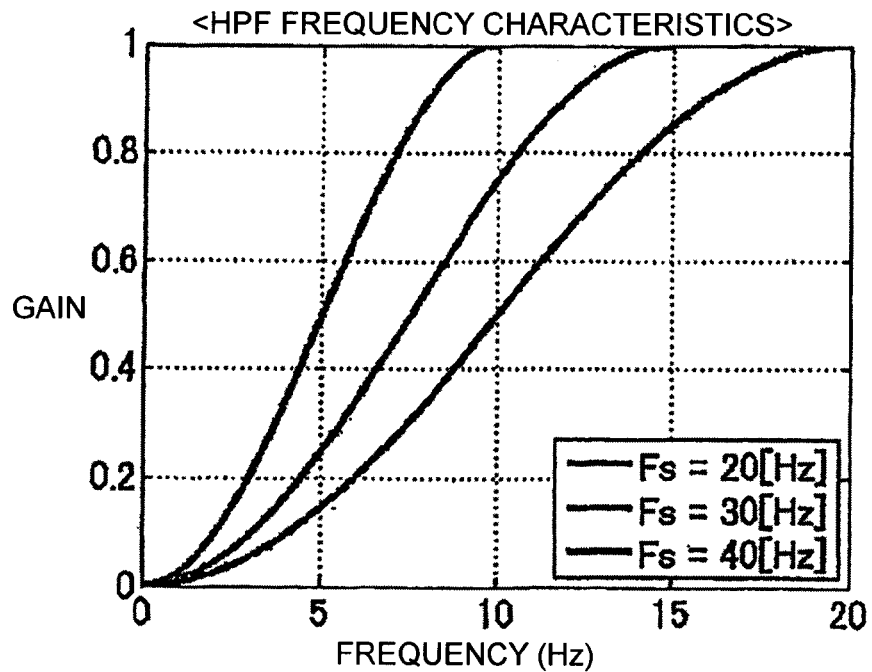
FIG. 9 Diagram illustrating change of the frequency characteristics of a HPF in accordance with a frame rate.

FIG. 9 illustrates changes of the frequency characteristics of a HPF in accordance with the frame rate, and specifically shows that the frequency characteristics of a HPF formed of a 3-tap FIR filter (FIG. 2) change in accordance with the frame rate. In FIG. 9, the horizontal axis shows the frequency and the vertical axis shows gain of a filter. In the graph, Fs denotes a frame rate (frame frequency), i.e. a sampling frequency of the frame data. Further, the frequency characteristics illustrated in FIG. 9 are obtained at each frame rate Fs, with the filter coefficients $k_{-1}$, $k_0$, and $k_1$ of the 3-tap FIR filter in FIG. 2 being set to −0.25, 0.50, and −0.25, respectively.

Figure 10:
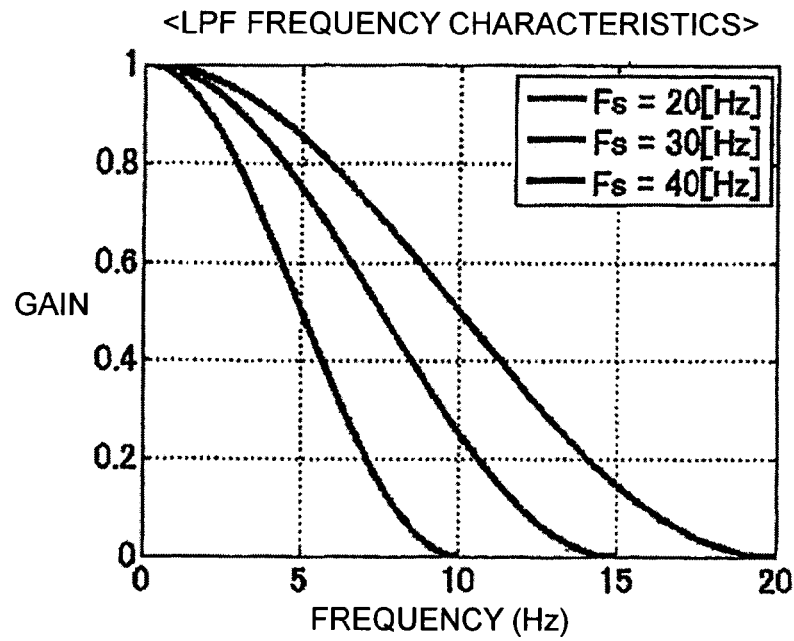
FIG. 10 Diagram illustrating change of the frequency characteristics of a LPF in accordance with a frame rate.

On the other hand, FIG. 10 illustrates changes of the frequency characteristics of a LPF in accordance with the frame rate, and specifically shows that the frequency characteristics of a LPF formed of a 3-tap FIR filter (FIG. 2) change in accordance with the frame rate. In FIG. 10, the horizontal axis shows the frequency and the vertical axis shows gain of a filter. In the graph, Fs denotes a frame rate (frame frequency), i.e. a sampling frequency of the frame data. Further, the frequency characteristics illustrated in FIG. 10 are obtained at each frame rate Fs, with the filter coefficients $k_{-1}$, $k_0$, and $k_1$ of the 3-tap FIR filter in FIG. 2 being set to 0.25, 0.50, and 0.25, respectively.

As illustrated in FIGS. 9 and 10, in a digital filter, if the filter coefficient is fixed, the frequency characteristics vary in accordance with the level of the frame rate Fs. Specifically, there is a tendency for the frequency characteristics to extend toward the frequency axis direction and the cutoff frequency to become higher as the frame rate Fs increases (becomes higher).

According to the present ultrasonic diagnostic apparatus, the filter coefficient of the digital filter illustrated in FIG. 2, for example, is adjusted in accordance with the level of the frame rate Fs which is set by a user operation, for example.

When the number of taps is fixed, the frequency characteristics of the HPF formed of the 3-tap FIR filter illustrated in FIG. 2, for example, are as shown in FIG. 3. FIG. 3 shows that as the filter coefficient $k_0$ increases from 0.5, the offset level of the HPF also increases. Further, as the offset level increases, the cutoff frequency of the HPF decreases. As such, it is possible to decrease the cutoff frequency of the HPF by increasing the offset level.

On the other hand, as has been described with reference to FIG. 9, there is a tendency that as the frame rate Fs increases, the frequency characteristics of the HPF are extended toward the frequency axis direction and the cutoff frequency increases. Namely, there is a tendency for the cutoff frequency to increase as the frame rate Fs increases.

Accordingly, in order to suppress the tendency that, as the frame rate Fs increases, the cutoff frequency also increases, the filter coefficient is adjusted such that as the frame rate Fs increases, the offset level is increased and the cutoff frequency is lowered. This adjustment allows control to prevent a change of the cutoff frequency of the HPF in accordance with the change of the frame rate Fs as much as possible. The filter coefficient of the HPF used in the HPF processing section 20 in FIG. 1 is adjusted by the filter setting section 22.

Also, when the number of taps is fixed, the frequency characteristics of the LPF formed of the 2-tap FIR filter illustrated in FIG. 2, for example, are as shown in FIG. 6. FIG. 6 shows that as the filter coefficient $k_0$ increases from 0.5, the offset level of the LPF also increases. Further, as the offset level increases, the cutoff frequency of the LPF increases. As such, it is possible to increase the cutoff frequency of the LPF by increasing the offset level.

On the other hand, as has been described with reference to FIG. 10, there is a tendency that as the frame rate Fs increases, the frequency characteristics of the LPF are extended toward the frequency axis direction and the cutoff frequency increases. Namely, there is a tendency for the cutoff frequency to increase as the frame rate Fs increases.

Accordingly, in order to suppress the tendency that, as the frame rate Fs increases, the cutoff frequency also increases, the filter coefficient is adjusted such that as the frame rate Fs increases, the offset level is decreased and the cutoff frequency is lowered. This adjustment allows control to prevent changes of the cutoff frequency of the LPF in accordance with the change of the frame rate Fs as much as possible. The filter coefficient of the LPF used in the post-processing section 40 in FIG. 1 is adjusted by the filter setting section 42.

Further, in addition to the filter coefficient, the number of taps of a filter may be adjusted. For example, if the frequency characteristics at the frame fate of 30 Hz are effective for reduction of the stationary echoes and suppression of flicker and blurring of an image in FIG. 9, the filter coefficient and the number of taps are adjusted so as to realize the frequency characteristics close to those at the frame rate of 30 Hz even when the frame rate is 40 Hz or 20 Hz. Specifically, if the frame rate is increased from 30 Hz to 40 Hz, for example, the filter coefficient and the number of taps are adjusted such that the cutoff frequency at 40 Hz is not high (such that the cutoff frequency approaches that at 30 Hz) and simultaneously the frequency characteristics at 40 Hz are not gentle (the frequency characteristics approach those at 30 Hz).

Similarly, if the frequency characteristics at the frame rate of 30 Hz are effective for suppression of flicker in FIG. 10, the filter coefficient and the number of taps are adjusted so as to realize the frequency characteristics close to those at the frame rate of 30 Hz even when the frame rate is 40 Hz or 20 Hz.

Figure 11:
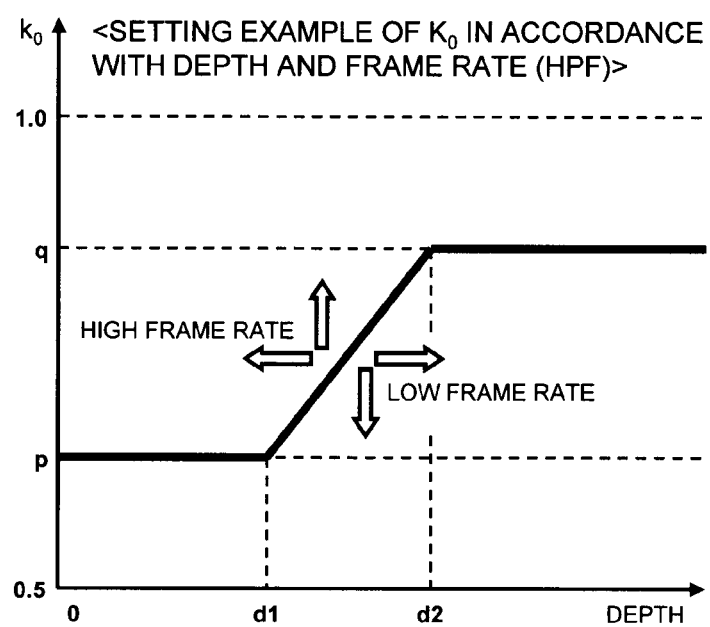
FIG. 11 View illustrating an example setting (HPF) of a filter coefficient $k_0$ in accordance with a depth and a frame rate.
Figure 12:
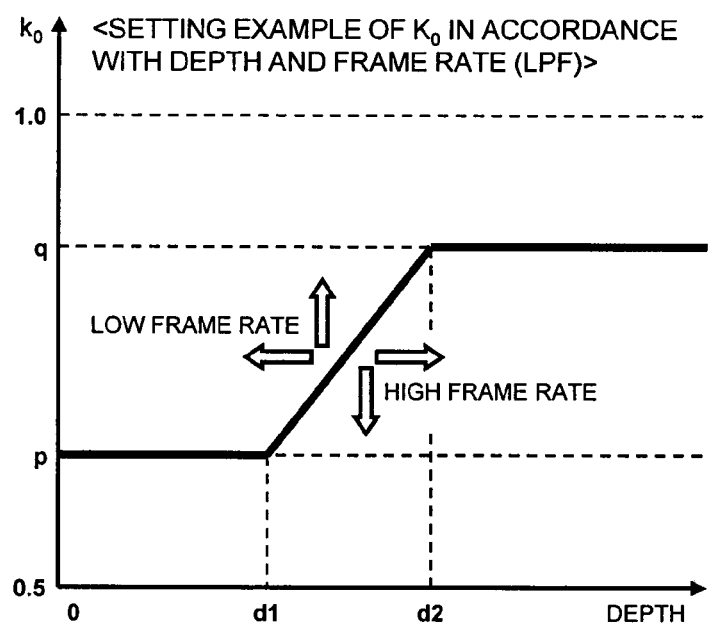
FIG. 12 View illustrating an example setting (LPF) of a filter coefficient $k_0$ in accordance with a depth and a frame rate.

Further, in order to establish both the control of the filter coefficient in accordance with the depth and the control of the filter coefficient in accordance with the frame rate in a HPF, the setting example illustrated in FIG. 11 can be considered. For example, in a case in which the characteristics of the filter coefficient $k_0$ in accordance with the depth are set at the reference frame rate (e.g. 30 Hz), when the frame rate is increased (to 40 Hz, for example), the characteristics of the filter coefficient $k_0$ of the HPF illustrated in FIG. 11 are shifted in a more superficial direction as a whole or in a direction in which the value of filter coefficient $k_0$ becomes larger as a whole. Of course, the shifts in both directions may be performed together. On the other hand, when the frame rate is decreased (to 20 Hz, for example), the characteristics of the filter coefficient $k_0$ of the HPF illustrated in FIG. 11 are shifted in a deeper direction as a whole or in a direction in which the value of filter coefficient $k_0$ becomes smaller as a whole. Of course, the shifts in both directions may be performed together Further, in order to establish both the control of the filter coefficient in accordance with the depth and the control of the filter coefficient in accordance with the frame rate in a LPF, the setting example illustrated in FIG. 12 can be considered. For example, in a case in which the characteristics of the filter coefficient $k_0$ in accordance with the depth are set at the reference frame rate (e.g. 30 Hz), when the frame rate is increased (to 40 Hz, for example), the characteristics of the filter coefficient $k_0$ of the LPF illustrated in FIG. 12 are shifted in a deeper direction as a whole or in a direction in which the value of filter coefficient $k_0$ becomes smaller as a whole. Of course, the shifts in both directions may be performed together. On the other hand, when the frame rate is deceased (to 20 Hz, for example), the characteristics of the filter coefficient $k_0$ of the LPF illustrated in FIG. 12 are shifted in a more superficial direction as a whole or in a direction in which the value of filter coefficient $k_0$ becomes larger as a whole. Of course, the shifts in both directions may be performed together.

With the above structure, it is possible to realize the reduction in the stationary echoes and the suppression of flicker and blurring of an image in the HPF processing section 20, and to further suppress flicker of the image in the post-processing section 40 while suppressing changes of the characteristics associated with the change of the frame rate.

The preferred embodiments of the present invention which have been described above are described only for the purpose of illustration, and do not limit the scope of the invention. The present invention may include various modifications without departing from the essence of the invention. The following are also preferable embodiments of the present invention.

Embodiment 1

An ultrasonic diagnostic apparatus, including a probe that transmits and receives ultrasound; a transmitter/receiver section that controls the probe to thereby obtain a reception signal of ultrasound; a filter processing section that applies filter processing to frame data obtained based on the reception signal of ultrasound along an arrangement direction of a plurality of frames; and an image forming section that forms an ultrasonic image based on the frame data having been subjected to the filter processing, wherein the filter processing section applies a high-pass filter having a filter coefficient set in accordance with a frame rate of frame data to the frame data, thereby performing the filter processing.

Embodiment 2

The ultrasonic diagnostic apparatus according to Embodiment 1, wherein the filter processing section applies a digital high-pass filter having a filter coefficient set such that the higher the frame rate, the higher the offset level.

Embodiment 3

The ultrasonic diagnostic apparatus according to Embodiment 1 or 2, wherein the filter processing section applies a digital high-pass filter having a greater number of taps as the frame rate increases.

Embodiment 4

The ultrasonic diagnostic apparatus according to any one of Embodiments 1 to 3, wherein the filter processing section applies a digital high-pass filter having a filter coefficient set in accordance with a frame rate of frame data and a depth of frame data within a frame to the frame data.

Embodiment 5

The ultrasonic diagnostic apparatus according to any one of Embodiments 1 to 4, further comprising a post-processing section that applies, to frame data having been processed in the filter processing section, a digital low-pass filter having a filter coefficient set in accordance with a frame rate along the arrangement direction of the plurality of frames.

Embodiment 6

The ultrasonic diagnostic apparatus according to Embodiment 5, wherein the post-processing section applies a digital low-pass filter having a filter coefficient set such that the lower the frame rate, the higher the offset level.

Embodiment 7

The ultrasonic diagnostic apparatus according to Embodiment 6, wherein the post-processing section applies a digital low-pass filter having a greater number of taps as the frame rate increases.

Embodiment 8

The ultrasonic diagnostic apparatus according to any one of Embodiments 5 to 7, wherein the post-processing section applies a digital low-pass filter, having a filter coefficient set in accordance with a frame rate of frame data and a depth of frame data within a frame, to the frame data.

REFERENCE SYMBOLS LIST 10 probe, 12 transmitter/receiver section, 20 HPF processing section, 40 post-processing section, 50 determination section.

The invention claimed is:
1. An ultrasonic diagnostic apparatus, comprising:
a probe that transmits and receives ultrasound;
a transmitter/receiver section that controls the probe to thereby obtain a reception signal of ultrasound;
a filter processing section that applies filter processing to frame data obtained based on the reception signal of ultrasound along an arrangement direction of a plurality of frames; and
an image forming section that forms an ultrasonic image based on the frame data having been subjected to the filter processing,
wherein the filter processing section applies a high-pass filter, having an offset level set in accordance with a depth within a frame, to frame data at the depth, thereby performing the filter processing, and wherein the filter processing section applies a high-pass filter having an offset level set to a higher level as the depth within a frame is greater and having characteristics closer to characteristics of an all-pass filter as the depth within a frame is greater.

2. An ultrasonic diagnostic apparatus, further comprising:
a probe that transmits and receives ultrasound;
a transmitter/receiver section that controls the probe to thereby obtain a reception signal of ultrasound;
a filter processing section that applies filter processing to frame data obtained based on the reception signal of ultrasound along an arrangement direction of a plurality of frames;
an image forming section that forms an ultrasonic image based on the frame data having been subjected to the filter processing; and
a post-processing section that applies a low-pass filter or a median filter to the frame data processed by the filter processing section along the arrangement direction of the plurality of frames,
wherein the filter processing section applies a high-pass filter, having an offset level set in accordance with a depth within a frame, to frame data at the depth, thereby performing the filter processing.

3. The ultrasonic diagnostic apparatus according to claim 2, wherein
the post-processing section, in a case of applying a low-pass filter, applies a low-pass filter, having an offset level set in accordance with a depth within a frame, to frame data at the depth.

4. The ultrasonic diagnostic apparatus according to claim 2, wherein
the post-processing section, in a case of applying a median filter, applies a median filter exclusively to frame data of a superficial region which is different from a deep region including a moving subject to be diagnosed.

5. The ultrasonic diagnostic apparatus according to claim 2, further comprising:
a determination section that confirms a change of the frame data processed by the filter processing section at each of locations within a frame along the arrangement direction of the plurality of frames, to thereby determine whether or not the processing performed by the post-processing section is necessary at a corresponding location.

6. The ultrasonic diagnostic apparatus according to claim 2, wherein
the post-processing section, in a case of applying a low-pass filter, applies a digital low-pass filter, having a filter coefficient set in accordance with a frame rate of frame data and a depth of frame data within a frame, to the frame data.

7. The ultrasonic diagnostic apparatus according to claim 6, wherein
the post-processing section applies a digital low-pass filter having a filter coefficient set such that the offset level is higher as the frame rate is lower.

8. The ultrasonic diagnostic apparatus according to claim 6, wherein
the post-processing section applies a digital low-pass filter having a larger number of taps as the frame rate is higher.

9. An ultrasonic diagnostic apparatus, comprising:
a probe that transmits and receives ultrasound;
a transmitter/receiver section that controls the probe to thereby obtain a reception signal of ultrasound;
a filter processing section that applies filter processing to frame data obtained based on the reception signal of ultrasound along an arrangement direction of a plurality of frames; and
an image forming section that forms an ultrasonic image based on the frame data having been subjected to the filter processing,
wherein the filter processing section applies a high-pass filter, having an offset level set in accordance with a depth within a frame, to frame data at the depth, thereby performing the filter processing, and
wherein the filter processing section applies a digital high-pass filter having a filter coefficient set in accordance with a frame rate of frame data and a depth of frame data within a frame to the frame data.

10. The ultrasonic diagnostic apparatus according to claim 9, wherein
the filter processing section applies a digital high-pass filter having a filter coefficient set such that the offset level is higher as the frame rate is higher.

11. The ultrasonic diagnostic apparatus according to claim 9, wherein
the filter processing section applies a digital high-pass filter having a larger number of taps as the frame rate is higher.

12. The ultrasonic diagnostic apparatus according to claim 10, wherein
the filter processing section applies a digital high-pass filter having a larger number of taps as the frame rate is higher.

* * * * *